United States Patent
Verbeke et al.

(10) Patent No.: US 11,144,596 B2
(45) Date of Patent: Oct. 12, 2021

(54) RETROACTIVE INFORMATION SEARCHING ENABLED BY NEURAL SENSING

(71) Applicant: Harman International Industries, Incorporated, Stamford, CT (US)

(72) Inventors: Joseph Verbeke, San Francisco, CA (US); Sven Kratz, Mountain View, CA (US); Stefan Marti, Oakland, CA (US)

(73) Assignee: Harman International Industries, Incorporated, Stamford, CT (US)

( * ) Notice: Subject to any disclaimer, the term of this patent is extended or adjusted under 35 U.S.C. 154(b) by 195 days.

(21) Appl. No.: 16/044,438

(22) Filed: Jul. 24, 2018

(65) Prior Publication Data
US 2020/0034492 A1   Jan. 30, 2020

(51) Int. Cl.
| | |
|---|---|
| G06F 17/00 | (2019.01) |
| G06F 7/00 | (2006.01) |
| G06F 16/9032 | (2019.01) |
| G06F 16/9535 | (2019.01) |
| G06F 16/635 | (2019.01) |
| G06F 40/40 | (2020.01) |
| G06F 3/01 | (2006.01) |
| G10L 15/22 | (2006.01) |
| G10L 15/24 | (2013.01) |
| G10L 15/26 | (2006.01) |

(52) U.S. Cl.
CPC ........ *G06F 16/90332* (2019.01); *G06F 3/015* (2013.01); *G06F 16/636* (2019.01); *G06F 16/9535* (2019.01); *G06F 40/40* (2020.01); *G10L 15/22* (2013.01); *G10L 15/24* (2013.01); *G10L 15/26* (2013.01); *G10L 2015/225* (2013.01)

(58) Field of Classification Search
CPC .......... G06F 16/90332; G06F 16/9535; G06F 16/636; G06F 40/40; G06F 3/015; G10L 15/22; G10L 15/24; G10L 15/26; G10L 2015/225
USPC ...................................................... 707/706
See application file for complete search history.

(56) References Cited

U.S. PATENT DOCUMENTS

| | | | |
|---|---|---|---|
| 8,671,069 B2 * | 3/2014 | Chang | G06N 5/02 706/52 |
| 9,762,851 B1 * | 9/2017 | Baumert | G06K 9/00671 |
| 9,886,953 B2 * | 2/2018 | Lemay | G10L 15/28 |
| 9,922,642 B2 * | 3/2018 | Pitschel | G10L 15/063 |
| 9,971,774 B2 * | 5/2018 | Badaskar | G06F 3/167 |
| 10,049,663 B2 * | 8/2018 | Orr | G10L 25/84 |
| 10,049,668 B2 * | 8/2018 | Huang | G10L 15/285 |

(Continued)

OTHER PUBLICATIONS

Extended European search report for application No. 19184430.7, dated Oct. 18, 2019.

(Continued)

*Primary Examiner* — Pavan Mamillapalli
(74) *Attorney, Agent, or Firm* — Artegis Law Group, LLP

(57) ABSTRACT

A method for retrieving information includes detecting a first neural activity of a user, wherein the first neural activity corresponds to a key thought of the user; in response to detecting the first neural activity, generating a search query based on speech occurring prior to detecting the first neural activity; retrieving information based on the search query; and transmitting the information to one or more output devices.

19 Claims, 8 Drawing Sheets

(56) References Cited

U.S. PATENT DOCUMENTS

| | | | |
|---|---|---|---|
| 10,061,843 B2* | 8/2018 | Hakkani-Tur | G06F 16/951 |
| 10,170,123 B2* | 1/2019 | Orr | G10L 17/22 |
| 10,311,871 B2* | 6/2019 | Newendorp | G06F 3/167 |
| 10,395,640 B1* | 8/2019 | Beach | G10L 15/01 |
| 10,606,897 B2* | 3/2020 | Gordner | G06F 16/951 |
| 10,610,111 B1* | 4/2020 | Tran | A61B 5/332 |
| 2002/0087525 A1* | 7/2002 | Abbott | G06F 16/9535 |
| | | | 707/999.003 |
| 2007/0016096 A1* | 1/2007 | McNabb | A61B 5/486 |
| | | | 600/545 |
| 2013/0339334 A1* | 12/2013 | Brown | G06F 16/9535 |
| | | | 707/706 |
| 2017/0068670 A1 | 3/2017 | Orr et al. | |
| 2017/0281086 A1 | 10/2017 | Donaldson | |
| 2019/0090771 A1* | 3/2019 | Kozhaya | A61B 5/165 |
| 2019/0336024 A1* | 11/2019 | Sgobba | A61B 5/04012 |

OTHER PUBLICATIONS

"Electroencephalography." En.wikipedia.org, at https://en.wikipedia.org/wiki/Electroencephalography. Jul. 21, 2018 revision retrieved on Mar. 12, 2020 from https://en.wikipedia.org/w/index.php?title=Electroencephalography&oldid=851342183, 31 pages.

Jacqui, Cheng, "Siri versus Google Voice Search: Fight!", Ars Technica, XP055798802, retrieved from the Internet URL: https://arstechnica.com/gadgets/2012/11/siri-versus-google-voice-search-fight/ Nov. 14, 2012, 3 pages.

* cited by examiner

RETROACTIVE INFORMATION SEARCHING ENABLED BY NEURAL SENSING

BACKGROUND

Field of the Embodiments

Embodiments of the present disclosure relate generally to computer information systems, and, more specifically, to retroactive information searching enabled by neural sensing.

Description of the Related Art

Smart phones, wearables, and other wireless devices enable a user to access the Internet and other information sources to retrieve information on essentially any subject. Freed from the necessity of a wired connection, a user can now perform an Internet search by opening a web browser on a smartphone or electronic tablet whenever wireless service is available. In addition, the widespread availability of intelligent personal assistants (IPAs), such as Microsoft Cortana™, Apple Siri™, and Amazon Alexa™, enable a user to initiate a search for information on a particular topic without even looking at a display screen or manually entering search parameters. Instead, the user can retrieve information from the Internet verbally by speaking a question to the IPA.

However, for a user to pull out a smartphone or speak to a digital assistant in the middle of a face-to-face conversation is generally regarded as socially rude behavior. In addition, searching for information relevant to an on-going conversation diverts the user's attention away from the conversation. Thus, by focusing on a particular aspect of the conversation and attempting to expand knowledge relevant to that aspect with an Internet search, the user can miss the overall thread of the conversation. Further, in the case of IPAs, verbally directing a question to an IPA-enabled device interrupts the conversation itself. Thus, while modern wireless devices and the Internet provide immediate access to a great deal of specific information on virtually any subject, taking advantage of such access in real-time and without disrupting an ongoing conversation can be problematic.

In light of the above, more effective techniques for enabling a user to discreetly access relevant information would be useful.

SUMMARY

The various embodiments set forth a method for providing information based on neural activity. The method includes detecting first neural activity of a user, wherein the first neural activity corresponds to a key thought of the user; in response to detecting the first neural activity, generating a search query based on speech occurring prior to detecting the first neural activity; receiving information based on the search query; and transmitting the information to an output device that privately outputs information to the user.

At least one advantage of the disclosed embodiments is that information relevant to an on-going conversation can be provided to a user in real-time. A further advantage is that relevant information can be provided to the user privately, for example, via headphones, earbuds, hearables, and/or a head-mounted display. Additionally, a search for relevant information can be initiated and performed in the background. Accordingly, relevant information can be retrieved and provided to the user without interrupting an on-going conversation.

BRIEF DESCRIPTION OF THE SEVERAL VIEWS OF THE DRAWINGS

So that the manner in which the above recited features of the various embodiments can be understood in detail, a more particular description of the various embodiments, briefly summarized above, may be had by reference to embodiments, some of which are illustrated in the appended drawings. It is to be noted, however, that the appended drawings illustrate only typical embodiments and are therefore not to be considered limiting of its scope, for the various embodiments may admit to other equally effective embodiments.

For clarity, identical reference numbers have been used, where applicable, to designate identical elements that are common between figures. It is contemplated that features of one embodiment may be incorporated in other embodiments without further recitation.

DETAILED DESCRIPTION

Figure 1:
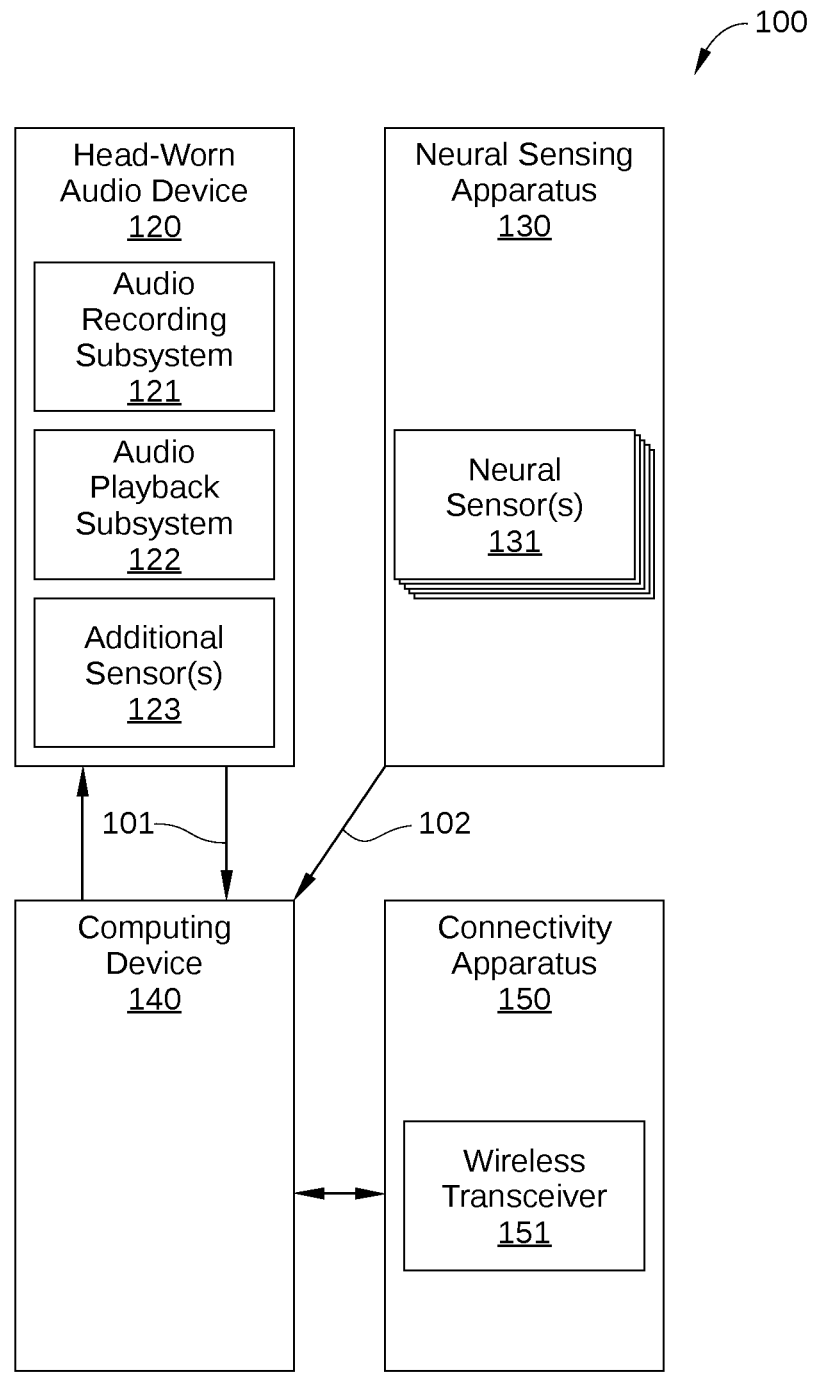
FIG. 1 is a schematic diagram illustrating a neural sensing-enabled information retrieval system, configured to implement one or more aspects of the various embodiments of the present disclosure.

FIG. 1 is a schematic diagram illustrating a neural sensing-enabled information retrieval system 100, configured to implement one or more aspects of the various embodiments of the present disclosure. Neural sensing-enabled information retrieval system 100 is configured to privately initiate a search for information related to an on-going conversation in which a user is engaged, and then present information to the user that is received in response to the search. Detection of specific neural activity in the user initiates the search, which is performed retroactively on topics and/or questions included in a conversation that was recorded prior to the detection of the specific neural activity. The neural activity is associated with that particular user when thinking a certain "key thought" in mind. Therefore, the search can be initiated unobtrusively and without interrupting the conversation. In addition, information received in response to the search can be presented via private audio, which also does not interrupt the conversation. Thus, neural sensing-enabled information retrieval system 100 effectively provides a user with "ambient omniscience" and "ambient knowledge injection" using a socially unobtrusive and subtle user interface method—human thought.

Neural sensing-enabled information retrieval system 100 includes a head-worn auditory device 120, a neural sensing apparatus 130, a computing device 140, and, in some embodiments, a connectivity apparatus 150. In some embodiments, head-worn auditory device 120, neural sensing apparatus 130, and/or computing device 140 are integrated into a single device, such as a headphone-based assembly. Alternatively, in some embodiments, head-worn auditory device 120, neural sensing apparatus 130, and/or computing device 140 are each separate physical devices. For example, in one such embodiment, head-worn auditory device 120 and neural sensing apparatus 130 are integrated into an earbud or pair of earbuds, while computing device 140 is implemented as a separate computing device, such as a smartphone or a wearable computing device.

Head-worn auditory device 120 can be any technically feasible head-worn or head-mountable device that includes an audio recording subsystem 121 (e.g., a microphone) and an audio playback subsystem 122 (e.g., a loud speaker). For example, in some embodiments, head-worn auditory device 120 can be configured as a headphone-based assembly, such as supra-aural headphones, which rest directly on the user's outer ear, or circumaural headphones, which completely surround the ears. In other embodiments, head-worn auditory device 120 can be configured as an earpiece/microphone assembly or as a single or a pair of earbuds. In some embodiments, head-worn auditory device 120 includes additional sensors 123, such as one or more inertial measurement units (IMUS) or other electronic devices that measure and report motion. In such embodiments, such additional sensors 123 can be coupled to the jaw of a user to enable detection of speech on the part of the user.

Audio recording subsystem 121 can include one or more microphones positioned to optimize the recording of the user's voice and generate audio data 101. Thus, audio recording subsystem 121 may include traditional over-air microphone technologies, bone-conduction microphones, and/or other transducer-based technology that converts sound into an electrical signal. Alternatively or additionally, audio recording subsystem 121 may include multiple microphones to enable beam forming, to further optimize the recording of a user's voice and/or the voices of other persons engaged in a conversation with the user.

Audio playback subsystem 122 includes any technically feasible loudspeakers or other audio playback device or devices that are worn by the user. For example, in some embodiments, audio playback subsystem 122 includes one or more in-ear, on-ear, over-ear, and/or bone-conductive loudspeakers. Alternatively, in some embodiments audio playback subsystem 122 is configured to provide private audio at a distance, for example, through speaker arrays ("hypersonic sound" and the like). In such embodiments, the loudspeakers of audio playback subsystem 122 may be located elsewhere on the user's body, rather than in head-worn auditory device 120.

Neural sensing apparatus 130 can be any technically feasible system or device configured to measure the neural activity of a user via one or more neural sensors 131. For example, in some embodiments, neural sensors 131 include one or more electroencephalography (EEG) sensors or other neural sensors for monitoring the surface electrical activity of a user's brain in real time. Typically, neural sensing apparatus 130 provides information about the user's neural activity via one or more EEG sensors (such as wet or dry electrodes) that are in contact with the user's scalp, face, or head at specific locations that are selected to monitor one or more specific regions of interest in the brain. In some embodiments, neural sensors 131 of neural sensing apparatus 130 can be integrated into head-worn auditory device 120 and/or can be worn as a separate assembly. In some embodiments, neural sensing apparatus 130 is configured to perform preprocessing of signals received from neural sensors 131, including noise reduction techniques, and to provide neural data 102 derived from such signals to computing device 140 for the monitoring of neural activity of the user and the detection of specific neural activity in the user. In some embodiments, neural sensing apparatus 130 is configured to record data derived from the signals received from neural sensors 131, while in other embodiments computing device 140 is configured to record such data.

Connectivity apparatus 150 is configured to provide wireless connectivity to external devices and/or networks, thereby enabling neural sensing-enabled information retrieval system 100 to search online for relevant questions and/or topics that have been extracted from recorded speech. As such, in some embodiments, connectivity apparatus 150 includes a wireless transceiver 151, such as a Bluetooth® transceiver, a WiFi transceiver, a wireless Internet transceiver and/or a transceiver compatible with a broadband cellular data network or satellite data network. Thus, in such embodiments, connectivity apparatus 150 enables connectivity to smartphones, electronic tablets, laptop computers, and the like, for additional computational resources and information. Alternatively or additionally, connectivity apparatus 150 enables connectivity to one or more wireless networks for accessing information via the Internet. For example, connectivity apparatus 150 enables connection to a remote server, where databases of information that is the subject of a search may be leveraged, and where training of an application or algorithm can be off-loaded for subsequent identification of the neural activity associated with the user thinking a specific key thought. In some embodiments, neural sensing-enabled information retrieval system 100 connects via connectivity apparatus 150 and a Bluetooth® connection to a user's smartphone, and routes search queries therethrough. Furthermore, in embodiments in which external output devices are included in or available to neural sensing-enabled information retrieval system 100, connectivity apparatus 150 can send information received in response to a search request to the appropriate external output device.

Computing device 140 is configured to perform various functions of neural sensing-enabled information retrieval system 100, including analyzing neural data 102 to recognize the neural activity associated with the user thinking a key thought, receiving and converting audio data 101 to text, performing textual content analysis, performing information searches, and presenting returned search information to the user. In addition, computing device 140 may be configured to interact with connectivity apparatus 150 to establish connection to the Internet and enable information searches and, in some embodiments, off-load computationally expensive tasks to a cloud-computing system.

Computing device 140 can be incorporated into head-worn auditory device 120. Alternatively, the functionality of computing device 140 can be incorporated into a mobile computing device, such as a suitably programmed smartphone, electronic tablet, smart watch, or other wearable. One embodiment of computing device 140 is described below in conjunction with FIG. 2.

Figure 2:
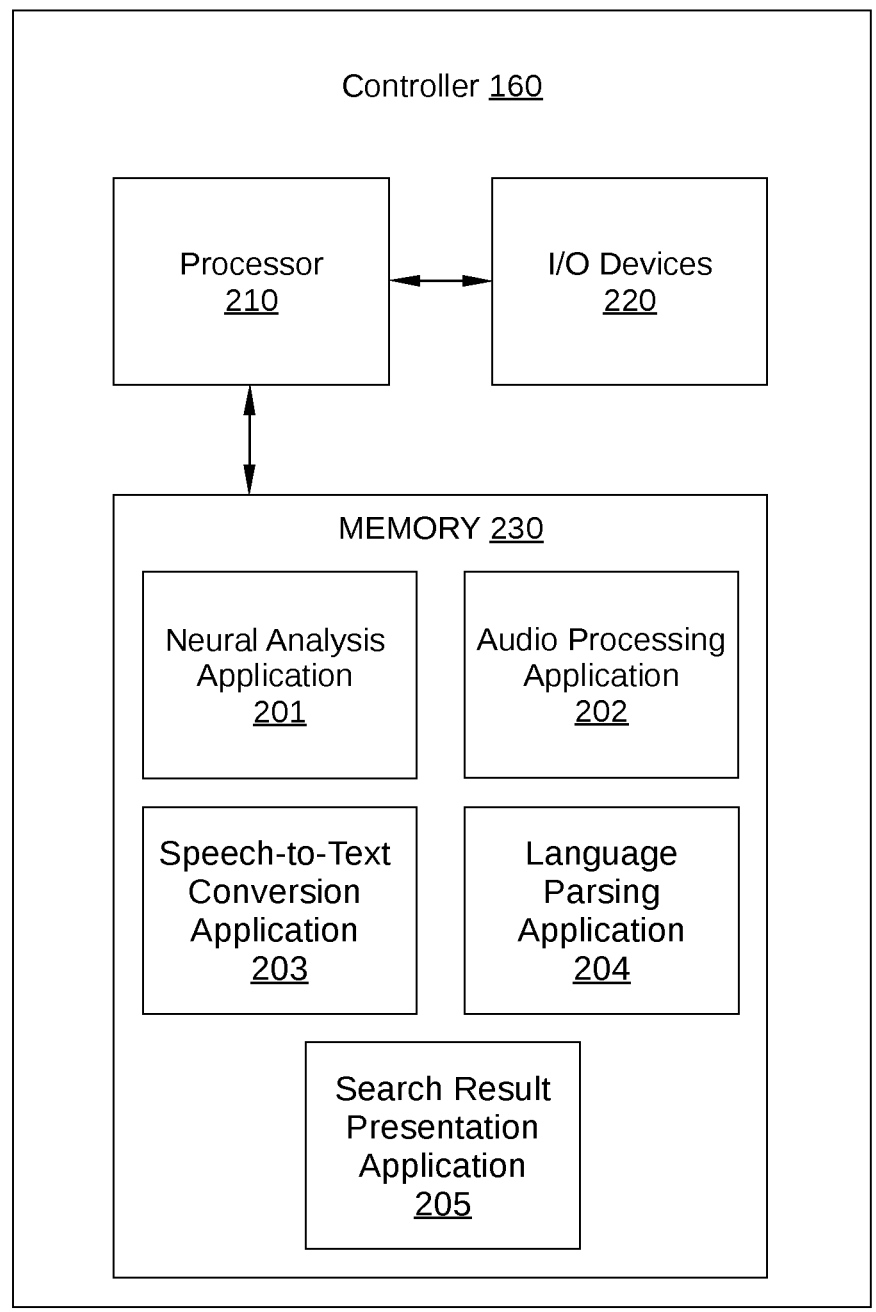
FIG. 2 is a more detailed illustration of a computing device in the neural sensing-enabled information retrieval system, according to various embodiments.

FIG. 2 is a more detailed illustration of computing device 140, according to various embodiments. Computing device 140 is configured to implement one or more aspects of the present disclosure described herein. Computing device 140 may be any type of device capable of executing application programs including, without limitation, instructions associated with a neural analysis application 201, an audio processing application 202, a speech-to-text conversion application 203, a language parsing program 204, and/or a search result presentation application 205. For example, and without limitation, computing device 140 may be an electronic tablet, a smartphone, a laptop computer, etc. Alternatively, computing device 140 may be implemented as a stand-alone chip, such as a microprocessor, or as part of a more comprehensive solution that is implemented as an application-specific integrated circuit (ASIC), a system-on-a-chip (SoC), and so forth. Generally, computing device 140 may be configured to coordinate the overall operation of a computer-based system, such as neural sensing-enabled information retrieval system 100. In other embodiments, computing device 140 may be coupled to, but separate from such a computer-based system. In such embodiments, the computer-based system may include a separate processor that transmits data to computing device 140, such as audio data 101 and/or neural data 102, and may be included in a consumer electronic device, such as a personal computer, smartphone, or headphone-based device. As shown, computing device 140 includes, without limitation, a processor 210, input/output (I/O) devices 220, and a memory 230.

Processor 210 may be implemented as a central processing unit (CPU), a graphics processing unit (GPU), an application-specific integrated circuit (ASIC), a field programmable gate array (FPGA), any other type of processing unit, or a combination of different processing units. In general, processor 210 may be any technically feasible hardware unit capable of processing data and/or executing software applications to facilitate operation of neural sensing-enabled information retrieval system 100 of FIG. 1, as described herein. Among other things, and without limitation, processor 210 may be configured to execute instructions associated with neural analysis application 201, audio processing application 202, speech-to-text conversion application 203, language parsing program 204, and/or search result presentation application 205.

Memory 230 may include a random access memory (RAM) module, a flash memory unit, or any other type of memory unit or combination thereof, and may include a single memory module or a collection of memory modules. As shown, in some embodiments, some or all of neural analysis application 201, audio processing application 202, speech-to-text conversion application 203, language parsing program 204, and/or search result presentation application 205 may reside in memory 230 during operation.

I/O devices 220 includes one or more devices capable of both receiving input, such as a keyboard, a mouse, a touch-sensitive screen, a microphone (including a microphone associated with audio recording subsystem 121) and so forth, as well as devices capable of providing output, such as a display screen, loudspeakers (including a loudspeaker associated with audio playback subsystem 122), and the like. The display screen may be incorporated in neural sensing-enabled information retrieval system 100 or may be external to neural sensing-enabled information retrieval system 100, such as a computer monitor, a video display screen, a display apparatus incorporated into a separate hand held device, or any other technically feasible display screen or projection device.

In operation, neural analysis application 201 analyzes neural data 102 to recognize the neural activity associated with the user thinking a key thought. For example, in some embodiments, neural analysis application 201 includes a neural activity detection algorithm. In some embodiments, neural analysis application 201 and/or computing device 140 receives an initial training (described below in conjunction with FIG. 5), so that the neural activity associated with a particular user thinking a specific key thought can be differentiated from other neural activity and, therefore, can be detected in real-time. Audio processing application 202 is employed by computing device 140 to perform post-processing on audio data 101 received from audio recording subsystem 121 to clean the audio signals included in audio data 101 and render voice portions of such audio signals to be more audible. For example, in some embodiments, audio processing application 202 includes voice isolation techniques and algorithms known in the art. Computing device 140 employs speech-to-text conversion application 203 for converting audio data 101 to text for subsequent parsing and analysis. Language parsing program 204 is employed by computing device 140 for analyzing textual content generated by speech-to-text conversion application 203 to determine questions, key words, and/or topics that can be included in search queries. Specifically, language parsing program 204 parses the textual content to detect explicit questions asked by the user and/or to determine search terms via context, frequency of use, and other language cues. In some embodiments, language parsing program 204 performs such parsing using common natural language understanding (NLU) and natural language processing (NLP) methods, as well as terminology extraction, discourse analysis, and the like. Search result presentation application 205 determines what is currently the preferred presentation mode of the information that is received in response to the search. For example, presentation application 205 determines the preferred presentation mode based on a specific input or selection from the user; whether information received in response to a search can be presented audibly and/or visually; what output mechanisms are available; what the current cognitive load on the user is; and/or whether the user is currently speaking.

Figure 3:
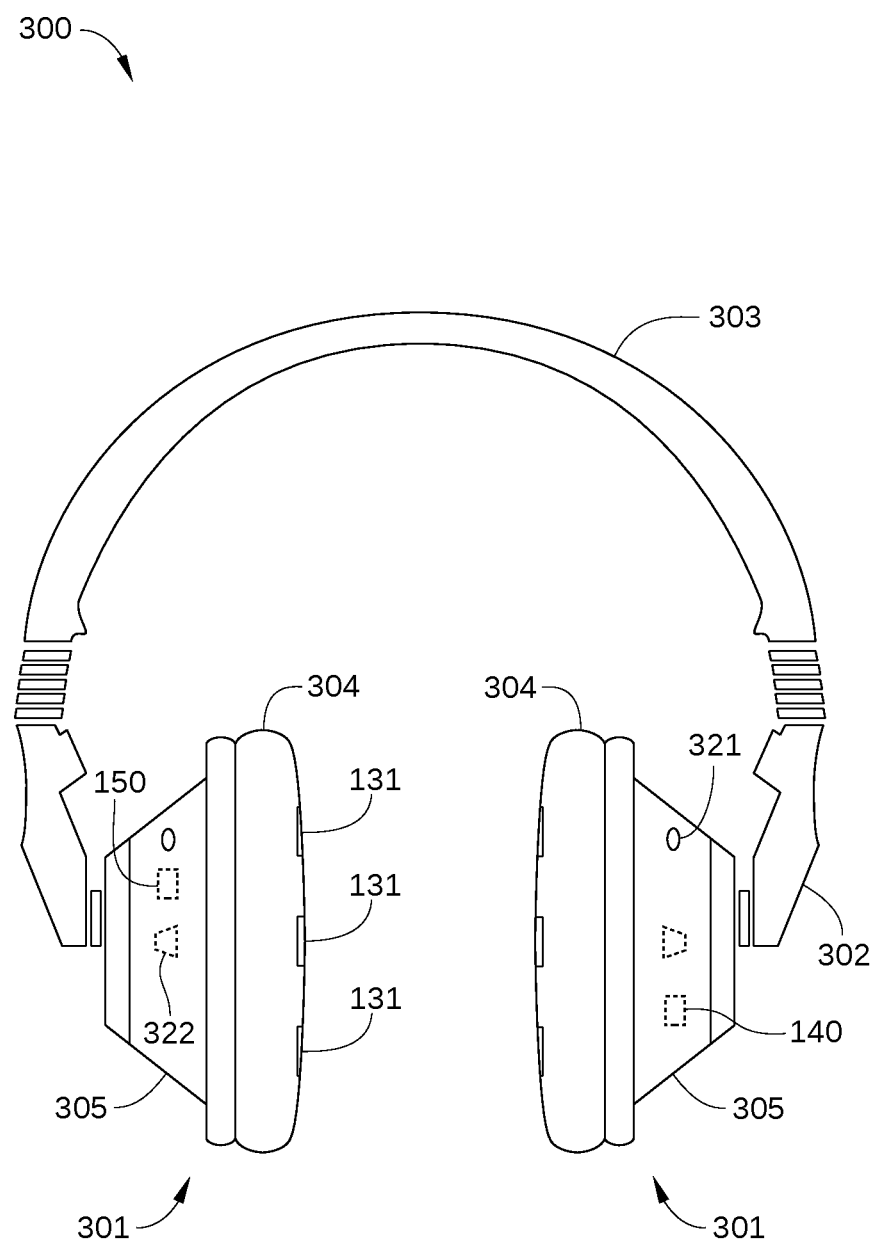
FIG. 3 is a schematic diagram illustrating a headphone system configured to implement one or more aspects of the disclosure.

In some embodiments, neural sensing-enabled information retrieval system 100 is implemented in a headphone-based assembly. One such embodiment is illustrated in FIG. 3. FIG. 3 is a schematic diagram illustrating a headphone system 300 configured to implement one or more aspects of the disclosure. Headphone system 300 may include, without limitation, two earcups 301, coupled to a headband 303 via a respective arm 302. Each earcup 301 is configured to fit over the outer ear of a user, when headphone system 300 is worn by the user, and includes, among other things, an ear-surround cushion 304 coupled to a housing 305. In some embodiments, headphone system 300 may be configured with a single earcup. Furthermore, in some embodiments, headphone system 300 may be configured as a supra-aural headphone system, while in other embodiments, headphone system 300 may be configured as a circumaural headphone system. In the embodiment illustrated in FIG. 3, headphone system 300 is configured as a circumaural headphone system.

As shown, head-worn auditory device 120 is incorporated into headphone system 300. Thus, included in earcups 301 are one or more microphones 321 of audio recording subsystem 121 (not shown), one or more loudspeakers 322 of audio playback subsystem 122 (not shown), and one or more neural sensors 131 of neural sensing apparatus 130 (not shown). In the embodiment illustrated in FIG. 3, neural sensors 131 are located in ear-surround cushions 304 to be in contact with specific locations on the head of a user when headphone system 300 is worn by the user. In some embodiments, neural sensors 131 are located in the headband 303. In some embodiments, computing device 140 and/or connectivity module 150 are disposed within housing 305 or headband 303.

When headphone system 300 is worn by a user, ear-surround cushion 304 seals against the user's head, so that each earcup 301 forms an acoustic cavity around one of the user's ears. By design, ear-surround cushion 304 forms and acoustically isolates this acoustic cavity from the surroundings for enhanced listening. In addition, neural sensors 131 are positioned to be in contact with specific locations on the head of the user, so that neural activity of the user can be measured and recorded.

Figure 4:
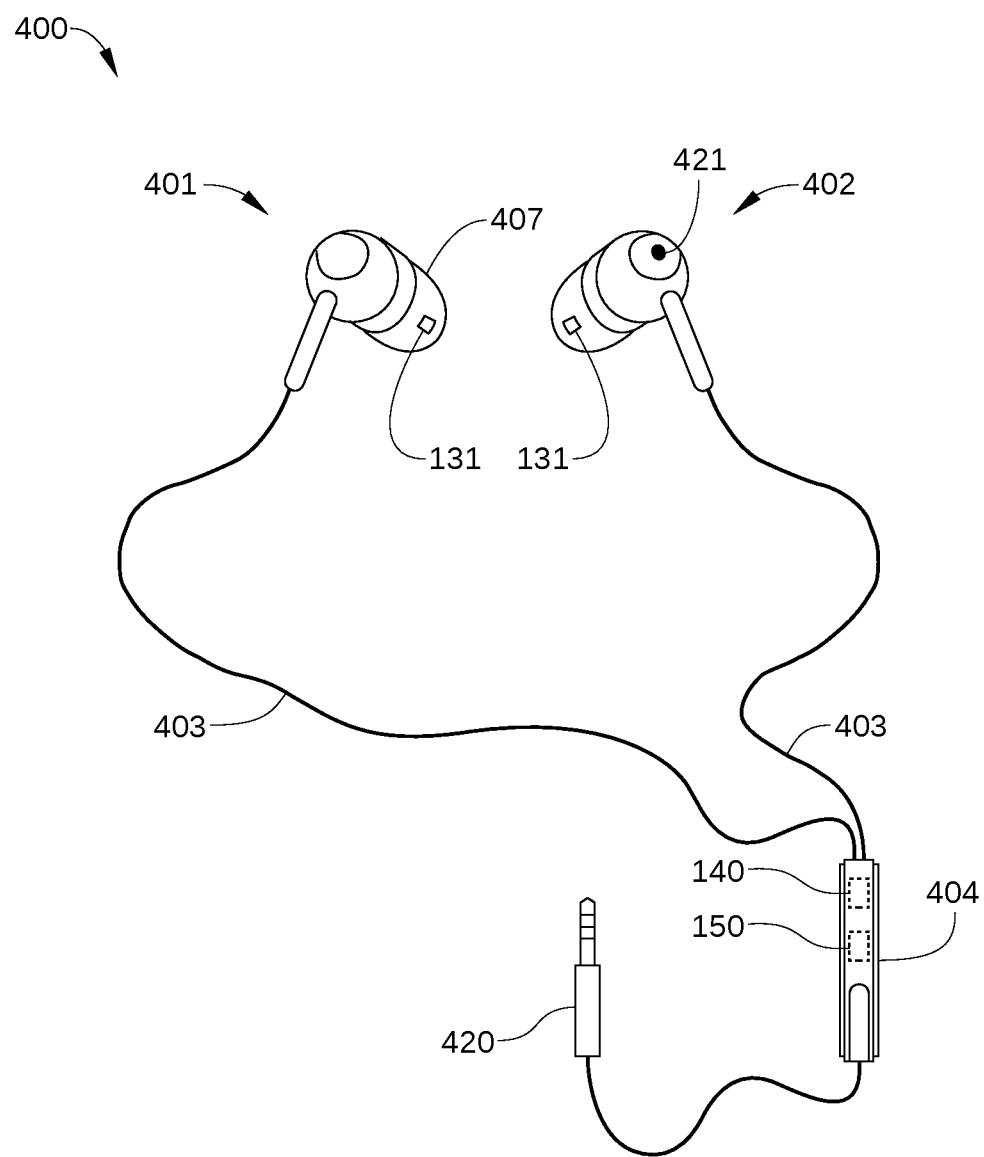
FIG. 4 is a schematic diagram illustrating a stereo earbud system configured to implement various aspects of the present disclosure.

In some embodiments, neural sensing-enabled information retrieval system 100 is implemented in an earbud-based assembly. One such embodiment is illustrated in FIG. 4. FIG. 4 is a schematic diagram illustrating a stereo earbud system 400 configured to implement various aspects of the present disclosure. Stereo earbud system 400 includes, without limitation, a left earbud 401 and a right earbud 402, each coupled to a plug assembly 420 via a wired connection 403. Alternatively, left earbud 401 and right earbud 402 may be configured as wireless earbuds. Stereo earbud system 400 may further include, without limitation, a volume control module 404 coupled to left earbud 401, right earbud 402, and plug assembly 420 as shown. Stereo earbud system 400 further includes, without limitation, neural sensors 131 disposed on a surface of left earbud 401 and/or right earbud 402. Thus, when a user has inserted left earbud 401 and right earbud 402, neural sensors 131 are positioned in contact with respective locations within the ear canal of the user, thereby enabling the measurement and recording of neural activity of the user. In addition, stereo earbud system 400 can further include, without limitation, one or more microphones 421.

In some embodiments, stereo earbud system 400 further includes, without limitation, one or more components of computing device 140 and/or connectivity apparatus 150. In such embodiments, the components of computing device 140 and/or connectivity apparatus 150 can be incorporated into left earbud 401, right earbud 402, and/or volume control module 404. Alternatively, components of computing device 140 and/or connectivity apparatus 150 can be incorporated into a device external to stereo earbud system 400. Alternatively, in some embodiments, stereo earbud system 400 can be configured as a mono earbud system with a single earbud or with two earbuds that produce identical audio output.

According to various embodiments, neural sensing-enabled information retrieval system 100 is configured to detect a user request for information while the user is engaged in a conversation, parse the verbal content of speech in the conversation that precedes the user request, search for relevant information and/or answers to questions, and deliver the information to the user. Such embodiments are described below in conjunction with FIGS. 5-8.

Figure 5:
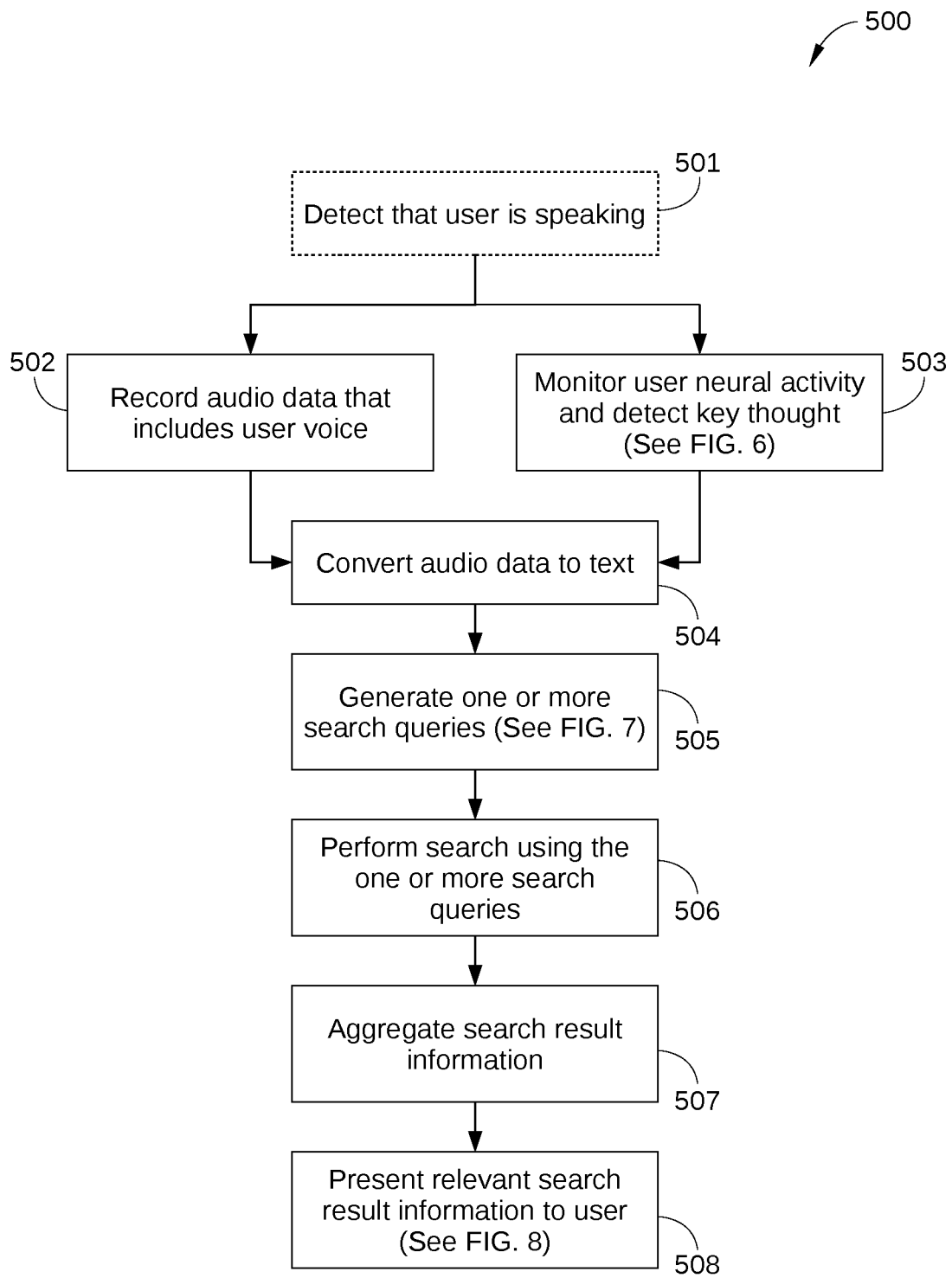
FIG. 5 sets forth a flowchart of method steps for providing information to a user based on neural activity, according to various embodiments of the present disclosure.

FIG. 5 sets forth a flowchart of method steps for searching for information, according to various embodiments of the present disclosure. Although the method steps are described with respect to the systems of FIGS. 1-4, persons skilled in the art will understand that any system configured to perform the method steps, in any order, falls within the scope of the various embodiments.

Prior to the method steps, computing device 140 and/or neural analysis application 201 undergoes a training process for detection of specific neural activity when a particular user is thinking a key thought. For example, in some embodiments the training process is performed as part of initial setup of neural sensing-enabled information retrieval system 100. In some embodiments, the training process includes measurement via neural sensors 131 of a user baseline state, in which the user attempts to think about nothing. Neural sensing-enabled information retrieval system 100 then prompts the user to think about a specific key thought for a set amount of time. This may include thinking of a word, color, object, piece of music, motion or action, etc. Generally, to reduce the likelihood of false triggers, the key thought selected by the user is something specific and unusual. After a sufficient time interval of thinking the key thought, neural analysis application 201 then analyzes and compares the recorded neural data 102 for each state. Differentiating patterns and features between the recorded neural data 102 for the baseline state and the key thought state are then used to create a classification or neural pattern that is associated with the user thinking the key thought. The classification or neural pattern can then be used to identify when the user is thinking of that particular key thought during operation of neural sensing-enabled information retrieval system 100.

In some embodiments, computing device 140 and/or neural analysis application 201 can be trained to recognize multiple different neural activities in the user, where each neural activity is associated with the user thinking a different respective key thought. In such embodiments, multiple different commands can be directed to neural sensing-enabled information retrieval system 100 by the user, rather than simply requesting a search for information pertinent to an on-going conversation. In some embodiments, the computational resources employed in such a training process can be off-loaded to a cloud-computing system.

As shown, a method 500 begins at optional step 501, in which audio recording subsystem 121 detects that the user is speaking. In response to detecting that the user is speaking, computing device 140 brings neural sensing-enabled information retrieval system 100 from a low-power state to a higher-power state. Specifically, in the low-power state, neural sensing apparatus 130 is powered off and one or more microphones included in audio recording subsystem 121 are on and generating audio data 101. In some embodiments, audio recording subsystem 121 records a small quantity of audio data 101 in a buffer sufficient to determine whether audio data 101 includes speech or other verbal utterances from the user, for example two to ten seconds of audio data 101. Alternatively, in some embodiments, recording subsystem 121 does not record any audio data 101 at all in the low-power state.

In some embodiments, audio recording system 121 detects that the user is speaking based on a sound volume of detected sound exceeding a minimum threshold level, since the voice of the user should be louder than that of others engaged in conversation with the user. Alternatively or additionally, in some embodiments, audio recording system 121 detects that the user is speaking based on another input, such as the detection of motion of the jaw of the user. In such embodiments, audio recording system 121 receives such an input from an IMU or other additional sensor(s) 123 included in head-worn auditory device 120.

In step 502, audio recording subsystem 121 operates in the higher-power state, and audio recording subsystem 121 records audio data 101 for subsequent analysis. In embodiments in which optional step 501 is included in method 500, audio recording subsystem 121 switches to the higher-power state in step 502. In embodiments in which optional step 501 is not included in method 500, audio recording subsystem 121 constantly operates in the higher-power state in step 502.

Generally, in the higher-power state, audio recording subsystem 121 records audio data 101 for a sufficient duration of time to enable subsequent detection of questions and/or key words that can be employed as search queries. For example, in some embodiments, audio recording subsystem 121 records up to about one minute to about five minutes of audio data 101 before overwriting older audio data 101. Generally, audio data 101 includes speech and/or other verbal utterances of the user and, in some embodiments, speech and/or verbal utterances of others engaged in conversation with the user. In some embodiments, audio processing application 202 is employed, for example by computing device 140, to perform post processing on audio signals included in audio data 101 to clean such signals and to extract the voice component or components. Furthermore, in some embodiments, audio recording subsystem 121 includes metadata for portions of audio data 101 indicating when the user is speaking, so that subsequent analysis of audio data 101 can be performed separately on user speech and on the speech of other participants in the conversation. Techniques for detecting whether the user is speaking or not is described above in conjunction with step 501.

In step 503, which is performed in parallel with step 502, neural sensing apparatus 130 operates in the higher-power state, and is powered on so that neural activity of the user can be monitored via neural sensors 131. In embodiments in which optional step 501 is included in method 500, neural sensing apparatus 130 is powered on in step 503. In embodiments in which optional step 501 is not included in method 500, neural sensing apparatus 130 constantly operates in the higher-power state in step 503.

In step 503, neural sensing apparatus 130 monitors user neural activity and detects neural activity in the user associated with the user thinking a specific key thought. Various embodiments of step 503 are described in conjunction with FIG. 6.

Figure 6:
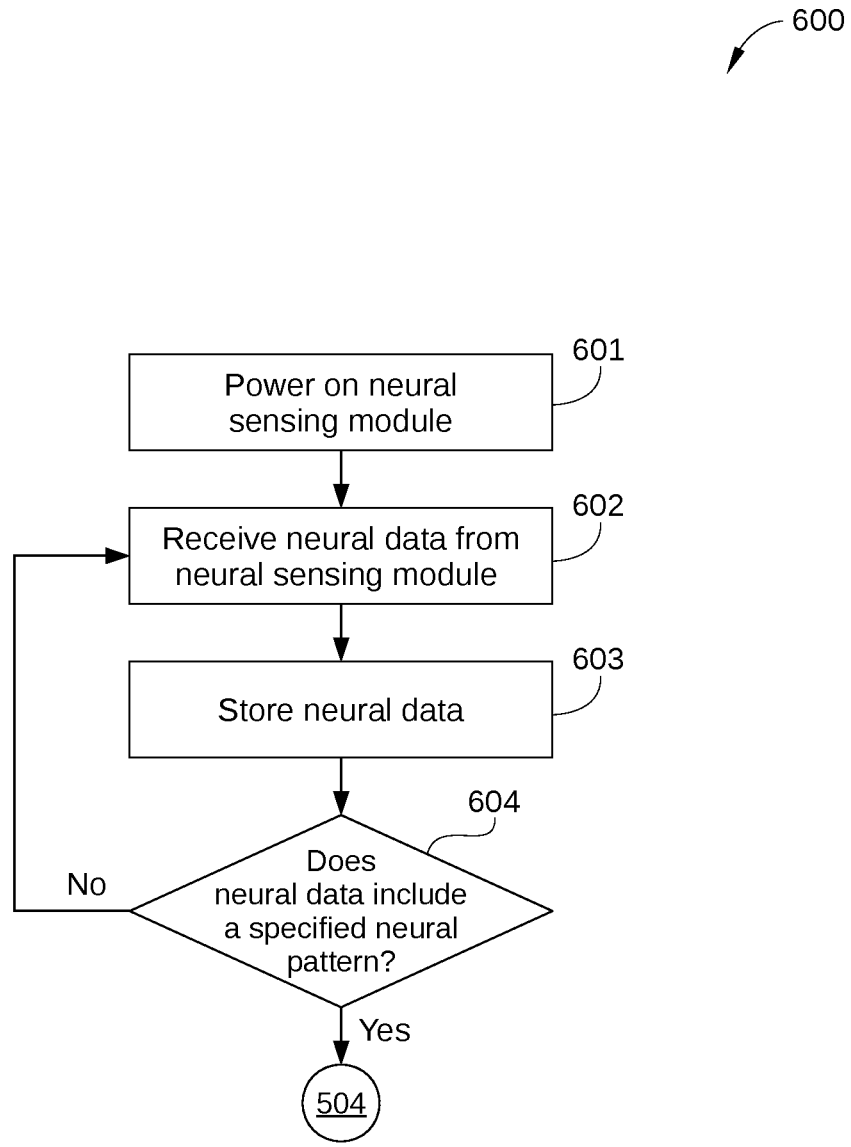
FIG. 6 sets forth a flowchart of method steps for detecting a neural activity in a user when the user thinks a specific thought, according to various embodiments of the present disclosure.

FIG. 6 sets forth a flowchart of method steps for detecting a neural activity in a user when the user thinks a specific thought, according to various embodiments of the present disclosure.

In step 601, computing device 140 causes neural sensing apparatus 130 to be powered on, for example, in response to detecting that the user has begun speaking. Neural sensing apparatus 130 then begins generating neural data 102. In some embodiments, neural data 102 are generated based on electrical measurements from neuron firings in the brain of the user. More specifically, in such embodiments, the electrical measurements are measurements of the neural activity occurring in one or more regions of the brain, rather than the electrical activity of a specific neuron or neurons in the brain of the user. Thus, the neural activity in the brain measured in step 601 is more than the neural activity associated with the firing of specifically targeted neurons. Instead, the neural activity measured is associated with an ensemble or aggregate activity in one or more specialized regions of brain. In addition, in such embodiments, the neural activity associated with multiple regions of the brain, and interactions therebetween, are measured. Thus, various components of neural activity associated with different functional regions of the brain can be monitored in step 601, such as certain emotional components, memory components, a component associated with mental effort currently being exerted by the user, etc. Therefore, the neural activity measured in step 601 varies depending on what specific thought or thoughts are currently in the mind of the user, and is not merely the measurement of the amplitude of one or more types of brainwaves, such as theta waves (4-7 Hz), alpha waves (8-15 Hz), beta waves (16-31 Hz), gamma waves (32-100 Hz), delta waves (0.1-3 Hz), and the like. For example, in some embodiments, neural data 102 includes time-transient information, and is therefore not limited to a repeating pattern of brainwaves.

In step 602, computing device 140 receives neural data 102 from neural sensing apparatus 130. Neural data 102 can be transmitted wirelessly to computing device 140 or via a wired connection. In some embodiments, neural data 102 received in step 602 are associated with a specific time period, for example the most recent few seconds of the current conversation. Alternatively, neural data 102 received in step 602 may be continuously streamed to computing device 140. In step 603, computing device 140 temporarily stores neural data 102, for example in a rotating buffer.

In step 604, computing device 140 analyzes the neural data 102 stored in step 604. In some embodiments, computing device 140 determines whether neural data 102 includes specific neural activity or pattern that is mapped to or otherwise associated with the user thinking a key thought. In particular, computing device 140 determines whether neural data 102 include the specific neural activity for which computing device 140 and/or neural analysis application 201 have undergone training to detect prior to method 500 being performed. In some embodiments, the specific neural activity is not limited to a repeating pattern and includes one or more time-transient components, since the act of thinking a key thought can include different components that vary over time. For example, the specific neural activity can include, without limitation, a memory component, an emotional component, a mental effort component, and the like, each of which can be engaged at a different intensity level at different times in the process of thinking a key thought. In some embodiments, the execution of neural analysis application 201 can be off-loaded to a cloud-computing system. If the stored neural data 102 include the specific neural activity, method 600 proceeds to step 504 in method 500; if the stored neural data 102 do not include the specific neural activity, method 600 proceeds back to step 602.

Returning to FIG. 5, in step 504 of method 500, computing device 140 converts audio data 101 to text. In some embodiments, speech-to-text conversion application 203 is employed, for example by computing device 140, to convert audio data 101 to text for subsequent parsing. In some embodiments, the execution of speech-to-text conversion application 203 can be off-loaded to a cloud-computing system.

In step 505, computing device 140 generates one or more search queries for information that is beneficial to the user in the context of the current conversation. Specifically, in some embodiments, computing device 140 performs analysis of the textual content generated in step 504 to determine what specific information the user has requested and/or for what topics the user can beneficially receive additional information. Various embodiments of step 505 are described in conjunction with FIG. 7.

Figure 7:
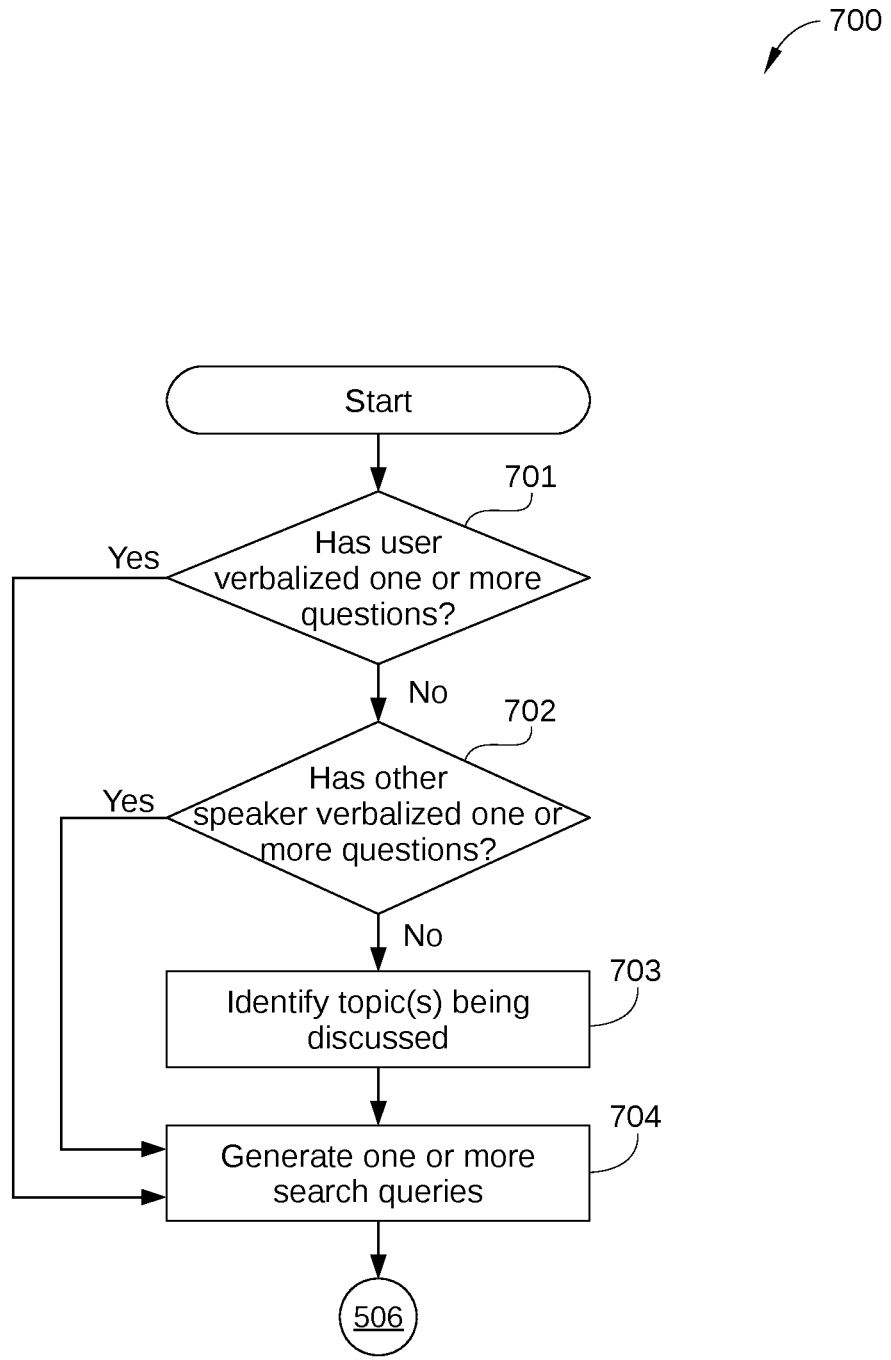
FIG. 7 sets forth a flowchart of method steps for generating one or more search queries in response to a request from the user for more information, according to various embodiments of the present disclosure.

FIG. 7 sets forth a flowchart of method steps for generating one or more search queries in response to a request from the user for more information, according to various embodiments of the present disclosure.

In step 701, computing device 140 determines whether the user has posed or verbalized one or more questions in the recent past. Specifically, computing device 140 determines whether the user's speech, during an appropriate time interval includes one or more questions. Generally, the appropriate time interval includes the time immediately prior to determining that neural data 102 includes a specific neural activity or pattern in step 604. For example, in some embodiments, the appropriate time interval equals the duration of time during which audio recording subsystem 121 has recorded audio data 101. Alternatively, in some embodiments, the appropriate time interval equals the most recently recorded portion of audio data 101, but not all of the recorded audio data 101. For example, in such an embodiment, audio data 101 includes the most recent five minutes of the current conversation, while the appropriate time interval equals the most recently recorded one minute of the current conversation. In such embodiments, if no question is detected in the appropriate time interval, a greater portion of the audio data can then be searched for a question. That is, the appropriate time interval is expanded or shifted earlier in time. If computing device 140 determines that the user's speech includes one or more questions in step 701, method 700 proceeds to step 704; if not, method 700 proceeds to step 702. In some embodiments, language parsing program 204 is employed by computing device 140 to perform the analysis of textual content in step 701. Alternatively, in some embodiments, the execution of language parsing program 204 can be off-loaded to a cloud-computing system.

In step 702, computing device 140 determines whether the speech of other speakers or participants in the conversation during the appropriate time interval includes one or more questions. As noted above, in some embodiments, a shorter time interval may first be employed in step 702 to search for questions, followed by a longer time interval. If computing device 140 determines that the speech of other speakers or participants in the conversation during the appropriate time interval includes one or more questions, method 700 proceeds to step 704; if no, method 700 proceeds to step 703. In some embodiments, language parsing program 204 is employed by computing device 140 to perform the analysis of textual content in step 702.

In step 703, which is performed in response to no explicit questions being detected in the most recent portion of the current conversation, computing device 140 performs a more thorough search of the recorded text from the current conversation to generate one or more search queries. In some embodiments, the search can be over a first time interval that occurs immediately before the key thought is detected (in step 503 of method 500), then over one or more additional time intervals that have occurred increasingly earlier in the current conversation. Computing device 140 identifies a key or primary topic and/or multiple topics that are included in the text corresponding to the first time interval and/or the additional time intervals. In some embodiments, text of the user's speech is employed in the search, while in other embodiments, text of the speech of other participants is also employed in the search. As noted above, language parsing program 204 generally parses the content of text generated in step 504 of method 500 to detect search terms via context, frequency of use, and other language cues. For example, if the user is having a conversation about politics and begins discussing President Trump's stance on renewable energy, the system will identify (through keywords, context, and other cues) the key themes of the portion of the current conversation preceding the request for information initiated by the user by thinking the key thought. Therefore, the keywords extracted for the search may be: "president," "Trump," "renewable energy," and "stance." These extracted search terms are employed as search queries in step 704.

In step 704, computing device 140 generates one or more search queries based on the questions detected in step 701 or 702, or on the search terms extracted in step 703. Method 700 then proceeds to step 506 of method 500. In the embodiment illustrated in FIG. 7, search queries are generated in step 704 based on one of questions verbalized by the user, questions verbalized by other speakers, or search terms extracted from a recorded portion of the conversation. Alternatively, in some embodiments, search queries generated in step 704 are based on any combination of questions verbalized by the user, questions verbalized by other speakers, and/or search terms extracted from a recorded portion of the conversation.

Returning to FIG. 5, in step 506 of method 500, computing device 140 performs one or more information searches using the search queries generated in step 704. As noted, the search queries can be based on explicit questions recently posed in the current conversation and/or on a topic or topics discussed in the current conversation. In some embodiments, the search or searches are performed locally, for example in a local database of information. Alternatively or additionally, in some embodiments, the search or searches are performed via a network, including the Internet.

In step 507, computing device 140 aggregates the search results received. For example, in some embodiments, computing device 140 ranks or arranges search results in order of relevance, eliminates redundant search results, and selects which search results received in response to performing the search of step 506 are to be presented to the user.

In some embodiments, the selection of content by computing device 140 may be determined by the output modality that will ultimately present the information to the user. Thus, in such embodiments, as part of the information aggregation process of step 507, computing device 140 determines what information output modalities are currently available to the user and discards or transforms information that cannot be presented to the user in the current state. For example, when only an audio output modality is available for presenting information to the user, such as loudspeakers included in audio playback subsystem 122, computing device 140 discards image-based information received as a search result, and can convert text-based information received into speech, via a text-to-voice application. In another example, an audio output modality may not be currently available for presenting information to the user but a visual output modality may be available, such as when computing device 140 has detected that the user is speaking or is listening to another participant, and neural sensing-enabled information retrieval system 100 includes a head-mounted display device. In such an example, computing device 140 can convert speech-containing audible information to text via speech-to-text conversion application 203, and present the text to the user via the head-mounted display device.

In step 508, computing device 140 presents selected search result information to the user. In some embodiments, search result presentation application 205 is employed, for example by computing device 140, to convert audio data 101 to text for subsequent parsing. In some embodiments, the execution of search result presentation application 205 can be off-loaded to a cloud-computing system.

Figure 8:
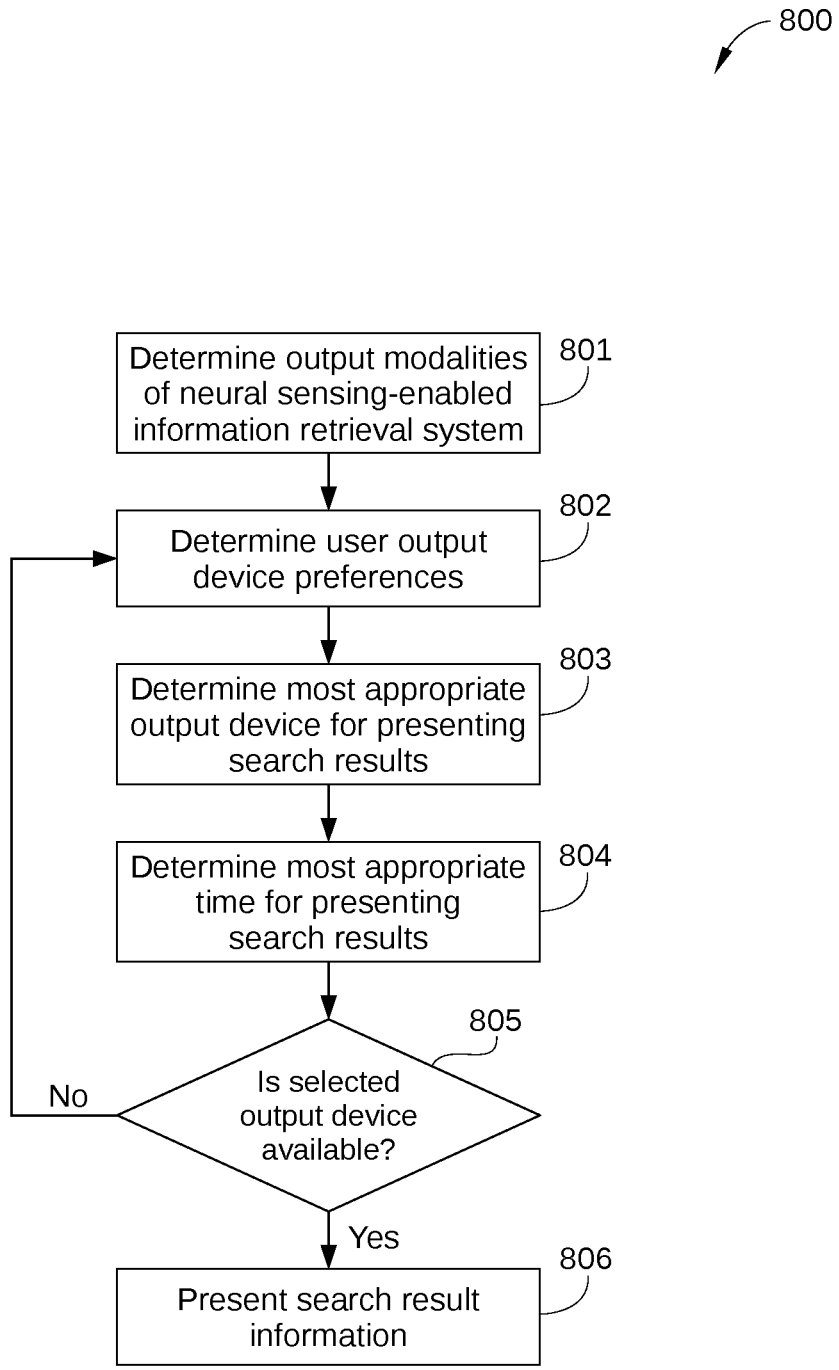
FIG. 8 sets forth a flowchart of method steps for presenting selected search result information to a user, according to various embodiments of the present disclosure.

In some embodiments, how and when computing device 140 presents selected search result information to the user may depend on one or more factors. A selection of such embodiments of step 508 are described in conjunction with FIG. 8. FIG. 8 sets forth a flowchart of method steps for presenting selected search result information to a user, according to various embodiments of the present disclosure.

In step 801, computing device 140 determines or looks up the output modalities of neural sensing-enabled information retrieval system 100 that are currently available, including audio output modalities and visual output modalities. For example, in embodiments in which neural sensing-enabled information retrieval system 100 is implemented in a headphone-based assembly or an earbud-based assembly, one audio output modality of neural sensing-enabled information retrieval system 100 is a private audio mode, in which only the user can hear the presentation of search result information. In embodiments in which loudspeakers external to neural sensing-enabled information retrieval system 100 are available to receive audio information from computing device 140, such as a smart speaker or electronic tablet wirelessly connected to neural sensing-enabled information retrieval system 100, another audio output modality is public audio mode, in which other participants in the conversation can also hear the presentation of search result information. In embodiments in which neural sensing-enabled information retrieval system 100 includes a head-mounted display device, one visual output modality of neural sensing-enabled information retrieval system 100 is a private visual mode, in which only the user can see the presentation of search result information. In embodiments in which a display device external to neural sensing-enabled information retrieval system 100 is available to receive image-based and/or video information from computing device 140, such as a computer display screen or digital projection system wirelessly connected to neural sensing-enabled information retrieval system 100, another visual output modality is public visual mode, in which other participants in the conversation can also see the presentation of search result information.

In step 802, computing device 140 determines or looks up what, if any, user output device preferences have been selected by the current user. In such embodiments, upon start-up and/or set-up of neural sensing-enabled information retrieval system 100, the user may be prompted to select one or more default output preferences. Examples of default output preferences include, without limitation, pausing audio presentation of search result information when the user is speaking; pausing audio presentation of search result information when anyone involved in the current conversation is speaking; providing search result information immediately; employing one of private audio mode (only audible to the user themselves, resulting in a "whispering" voice interface), public audio mode (audible to the user and people in proximity of the user), private video mode, or public video mode as the default output mode; and the like.

In step 803, computing device 140 determines the most appropriate output device for the search result information to be presented. The most appropriate output device selected by computing device 140 can be based on multiple factors. Examples of such factors include, without limitation, the output modalities determined to be available in step 801; user selections determined in step 802; the content of the search result information (i.e., audio or visual); and the like.

In step 804, computing device 140 determines the most appropriate time to present the search result information. The most appropriate time determined by computing device 140 can be based on multiple factors. Examples of such factors include, without limitation, user selections determined in step 802; whether the user is speaking; whether other participants in the conversation are speaking; complexity of search result information to be presented (including quantity of and number of output modes associated with the search result information); current cognitive load on the user (based on information in neural data 102, such as indications that the user listening to another participant in the conversation); whether the appropriate output device is currently being used for a different task; and the like.

In step 805, computing device 140 determines whether the most appropriate output device selected in step 803 is available at the most appropriate time determined in step 804. If yes, method 800 proceeds to step 806; if no, method 800 repeats step 805.

In step 806, computing device 140 presents the search result information via the most appropriate output device to the user or to all participants in the conversation, as appropriate. In addition, computing device 140 presents the search result information at the most appropriate time.

In some embodiments of method 500, search queries are generated, searches performed, and search results aggregated via an intelligent personal assistants (IPAs), such as Microsoft Cortana™, Apple Siri™, and Amazon Alexa™. Thus, in such embodiments, steps 505, 506, and 507 (and in some embodiments also step 504) are performed by an IPA. For example, when computing device 140 determines that stored neural data 102 include the specific neural activity, in lieu of performing step 504 ("Convert audio data to text"), computing device 140 transmits an appropriate recorded snippet, e.g., audio data 101, to a suitable IPA. The IPA then performs functions roughly equivalent to steps 505, 506, and 507, and returns aggregated or otherwise filtered and organized search results to computing device 140. Computing device 140 then presents relevant search result information to the user, as described above in step 508.

Alternatively, in some embodiments, before transmitting audio data 101 to the IPA, computing device 140 performs certain pre-analysis and/or trimming, clipping, or other modifications on audio data 101, in lieu of step 504 ("Convert audio data to text"). For example, when a key thought is detected in step 503, computing device 140 then detects segments of recorded audio within audio data 101 which have the characteristics of spoken language questions. In some embodiments, sentence boundaries are first detected, for example by finding pauses in the audio signal, then questions are detected by finding certain pitch contours that indicate a question in the language being spoken. For example, in English, rising voice pitch at the end of a sentence generally indicates a question is being asked. Thus, in such embodiments, computing device 140 can employ both pause detection and pitch detection, which are different from speech recognition, to detect questions to be forwarded to the IPA.

Embodiments of method 500 enable a user to quickly and easily initiate a search for information relevant to a currently on-going discussion without the interruption associated with consulting a smartphone or speaking to a digital personal assistant. In addition, the embodiments enable the search result information to be selectively received either privately or publicly. For example, in one instance, a user is in an engineering brainstorm with a team from another company. The conversation so far has been on topics that the user has prepared for, or already has knowledge of, but then the conversation shifts to an area the user is less knowledgeable about. Thus, the user would benefit from additional information about the topic being discussed, but cannot access a computer or smartphone or open a dialogue with a voice agent during the meeting without interrupting the current conversation. Instead, the user responds to a question to the best of his or her knowledge, then immediately thinks or holds in mind the key thought for which neural sensing-enabled information retrieval system 100 has been trained to detect the associated neural activity. Neural sensing-enabled information retrieval system 100 detects the neural activity associated with the key thought, parses the content of recent user speech (and in some embodiments other speech), and performs a search related to the topic being discussed. By the time the user has finished talking, neural sensing-enabled information retrieval system 100 has found and is ready to deliver relevant search result information. In one embodiment, the information is immediately displayed privately to the user on a head-mounted display device worn by the user. In another embodiment, the relevant search result information is "whispered" privately to the user via one or two earbud speakers as soon as the user has stopped talking. Thus, the user can then immediately begin reviewing (or reading aloud) some or all of the relevant search result information.

In some embodiments, neural sensing-enabled information retrieval system 100 can be configured to perform a different operation than initiating a search in response to detecting a specific neural activity associated with a key thought. For example, in one such embodiment, neural sensing-enabled information retrieval system 100 can be configured to record an audio snippet of the current conversation for subsequent transcription. In another such embodiment, neural sensing-enabled information retrieval system 100 can be configured to perform a fact-checking function in response to detection a specific neural activity in the user. Thus, rather than determining whether recent speech of participants in the conversation includes one or more questions, computing device 140 parses a recent portion of the conversation for answered questions and/or stated facts, and then checks the validity thereof via a search for relevant information. In some embodiments, the fact-checking function is performed on questions answered and/or facts stated by the user. Alternatively or additionally, the fact-checking function is performed on questions answered and/or facts stated by other participants in the conversation.

In the embodiments described above in conjunction with FIGS. 5-8, neural sensing-enabled information retrieval system 100 is configured to operate in response to detecting a single neural activity that is associated with a key thought being held in the mind of a particular user. In other embodiments, neural sensing-enabled information retrieval system 100 can be configured to operate in response to detecting one of multiple different neural activities, each of which is associated with a different respective key thought being held in the mind of one particular user. In such embodiments, a training process for computing device 140 and/or neural analysis application 201 includes the detection of a specific neural activity for each of the different key thoughts being held in the mind of that particular user. In such embodiments, each of the key thoughts can be contrasted against a user baseline state, for example when the user attempts to think about nothing. Furthermore, in such embodiments, computing device 140 can be configured to perform a different action or process in response to detecting each of the different neural activities. For example, in some embodiments, detection of a first key thought causes computing device 140 to privately initiate a search for information relevant to the current conversation, as described above; detection of a second key thought causes computing device 140 to change a default output modality (for example, presenting relevant search information only when the user is not speaking); detection of a third key thought causes computing device 140 select a particular output device as the default output device; detection of a fourth key thought causes computing device 140 to perform a fact-checking function; detection of a fifth key thought causes computing device 140 to record an audio snippet of the current conversation for subsequent transcription; and so on.

In sum, various embodiments set forth systems and techniques for searching for information in real time. In response to detecting a neural activity in a user associated with the user thinking a specific key thought, a computing device generates one or more search queries and initiates a search using the one or more search queries. The search queries are based on verbal utterances from a conversation that are recorded prior to detecting the specific neural activity. Information received as a result of the search queries can be presented privately to the user or publicly to other participants in the conversation.

At least one technological improvement of the disclosed embodiments is that a user can privately initiate a search for information relevant to an on-going conversation in real time and without interrupting an on-going conversation. A further technological improvement is that relevant search result information can be delivered seamlessly and privately to the user, in real time and without interrupting an on-going conversation. Yet another technological improvement is that the user can be provided with the appearance of "ambient omniscience" to the outside world, since the user can privately and unobtrusively access information that is available online during an on-going conversation.

1. In some embodiments, a non-transitory computer-readable storage medium includes instructions that, when executed by one or more processors, configure the one or more processors to retrieve information by performing the steps of: detecting first neural activity of a user, wherein the first neural activity corresponds to a key thought of the user; in response to detecting the first neural activity, generating a search query based on speech occurring prior to detecting the first neural activity; receiving information based on the search query; and transmitting the information to one or more output devices.

2. The non-transitory computer-readable storage medium of clause 1, wherein detecting the first neural activity comprises: receiving an output from a neural sensor that measures neural activity of the user; and identifying the first neural activity in the output.

3. The non-transitory computer-readable storage medium of clauses 1 or 2, wherein the neural sensor includes an electroencephalography (EEG) device.

4. The non-transitory computer-readable storage medium of any of clauses 1-3, further including instructions that, when executed by one or more processors, configure the one or more processors to perform the step of training a neural analysis application to detect the first neural activity while the user is thinking the key thought, wherein the first neural activity is detected by the neural analysis application.

5. The non-transitory computer-readable storage medium of any of clauses 1-4, wherein detecting the first neural activity is performed by a cloud-based computing system.

6. The non-transitory computer-readable storage medium of any of clauses 1-5, further including instructions that, when executed by one or more processors, configure the one or more processors to perform the step of determining a preferred presentation mode, wherein the one or more output devices correspond to the preferred presentation mode.

7. The non-transitory computer-readable storage medium of any of clauses 1-6, wherein determining the preferred presentation mode comprises one or more of determining a default presentation mode of the information, determining one or more hardware devices that are currently available for outputting the information, determining whether the information has a visual component, and determining whether the information has an audio component.

8. The non-transitory computer-readable storage medium of any of clauses 1-7, further including instructions that, when executed by one or more processors, configure the one or more processors to further perform the steps of: determining that the user is speaking; and in response, initiating recording of speech, wherein determining that the user is speaking comprises at least one of detecting motion of a jaw of the user and detecting speech at a volume exceeding a threshold level.

9. The non-transitory computer-readable storage medium of any of clauses 1-8, wherein the speech includes at least one of speech by the user and speech by a person in conversation with the user.

10. The non-transitory computer-readable storage medium of any of clauses 1-9, wherein generating the search query based on the speech recorded prior to detecting the first neural activity comprises: converting the speech to text; and extracting search terms from the text, wherein the search query includes the one or more search terms.

11. The non-transitory computer-readable storage medium of any of clauses 1-10, wherein transmitting information received in response to the search to the one or more output devices comprises: determining a time indicated by the user to transmit the information received in response to the search; and transmitting the information received in response to the search at the time indicated by the user to one or more output devices.

12. The non-transitory computer-readable storage medium of any of clauses 1-11, wherein transmitting information received in response to the search to the one or more output devices comprises: determining an output time that comprises one of a time when no speech is detected, a time immediately after receiving the information in response to the search, and a time when a cognitive load on the user is less than a threshold level; and transmitting the information received in response to the search at the output time.

13. The non-transitory computer-readable storage medium of any of clauses 1-12, wherein transmitting the information received in response to the search to the one or more output devices comprises one of transmitting the information received in response to the search to an output device that privately outputs information to the user and transmitting the information received in response to the search to an output device that publicly outputs information.

14. In some embodiments, a method for providing information based on neural activity comprises: detecting first neural activity of a user, wherein the first neural activity corresponds to a key thought of the user; in response to detecting the first neural activity, generating a search query based on speech occurring prior to detecting the first neural activity; receiving information based on the search query; and transmitting the information to an output device that privately outputs information to the user.

15. The method of clause 14, wherein generating the search query based on the speech recorded prior to detecting the first neural activity comprises: converting the speech to text; and identifying one or more questions in the text.

16. The method of clauses 14 or 15, further comprising: detecting a second neural activity of the user; and in response to detecting the first neural activity, performing one of a fact-checking function on speech occurring prior to detecting the second neural activity and recording speech occurring after detecting the second neural activity.

17. In some embodiments, a system comprises: a neural sensor included in a head-worn assembly; and a processor coupled to the neural sensor and configured to: receive neural data from the neural sensor; detect, based on the neural data, a first neural activity of a user, wherein the first neural activity corresponds to a key thought of the user; in response to detecting the first neural activity, generate a search query based on speech occurring prior to detecting the first neural activity; receive information based on the search query; and transmit the information to an output device.

18. The system of clause 17, wherein the neural sensor includes an electroencephalography (EEG) device.

19. The system of clauses 17 or 18, wherein the head-worn assembly comprises one of a headphone-based assembly and an earbud-based assembly.

20. The system of any of clauses 17-19, wherein the output device comprises one of a loudspeaker included in the head-worn assembly and a display device included in the head-worn assembly.

Any and all combinations of any of the claim elements recited in any of the claims and/or any elements described in this application, in any fashion, fall within the contemplated scope of the present invention and protection.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments.

Aspects of the present embodiments may be embodied as a system, method or computer program product. Accordingly, aspects of the present disclosure may take the form of an entirely hardware embodiment, an entirely software embodiment (including firmware, resident software, microcode, etc.) or an embodiment combining software and hardware aspects that may all generally be referred to herein as a "module" or "system." In addition, any hardware and/or software technique, process, function, component, engine, module, or system described in the present disclosure may be implemented as a circuit or set of circuits. Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Aspects of the present disclosure are described above with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, enable the implementation of the functions/acts specified in the flowchart and/or block diagram block or blocks. Such processors may be, without limitation, general purpose processors, special-purpose processors, application-specific processors, or field-programmable processors or gate arrays.

The flowchart and block diagrams in the figures illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

While the preceding is directed to embodiments of the present disclosure, other and further embodiments of the disclosure may be devised without departing from the basic scope thereof, and the scope thereof is determined by the claims that follow.

What is claimed is:

1. A non-transitory computer-readable storage medium including instructions that, when executed by one or more processors, configure the one or more processors to retrieve information by performing the steps of:
    detecting speech;
    detecting a first neural activity of a user via one or more neural sensors that measure neural activity of one or more brain regions of the user;
    determining, via a neural analysis application, that the user is thinking a key thought based on the detected first neural activity, wherein the neural analysis application analyzes the first neural activity to determine that the first neural activity is associated with the user thinking the key thought, wherein the neural analysis application is configured to differentiate the first neural activity from other neural activity of the user;
    in response to determining that the user is thinking the key thought, generating a search query based on the speech occurring during a predetermined time period prior to determining that the user is thinking the key thought;
    receiving information based on the search query; and
    transmitting the information to one or more output devices.

2. The non-transitory computer-readable storage medium of claim 1, wherein detecting the first neural activity comprises:
    receiving an output from the one or more neural sensors that measure neural activity of the user; and
    identifying the first neural activity in the output.

3. The non-transitory computer-readable storage medium of claim 2, wherein the one or more neural sensors includes one or more electroencephalography (EEG) devices.

4. The non-transitory computer-readable storage medium of claim 2, wherein determining that the user is thinking the key thought is performed by a cloud-based computing system executing the neural analysis application.

5. The non-transitory computer-readable storage medium of claim 1, further including instructions that, when executed by the one or more processors, configure the one or more processors to perform the step of determining a preferred presentation mode, wherein the one or more output devices correspond to the preferred presentation mode.

6. The non-transitory computer-readable storage medium of claim 5, wherein determining the preferred presentation mode comprises one or more of determining a default presentation mode of the information, determining one or more hardware devices that are currently available for outputting the information, determining whether the information has a visual component, or determining whether the information has an audio component.

7. The non-transitory computer-readable storage medium of claim 1, further including instructions that, when executed by the one or more processors, configure the one or more processors to further perform the steps of:
    determining that the user is speaking; and
    in response, initiating recording of the speech, wherein determining that the user is speaking comprises at least one of detecting motion of a jaw of the user or detecting speech at a volume exceeding a threshold level.

8. The non-transitory computer-readable storage medium of claim 7, wherein the speech includes at least one of speech by the user or speech by a person in conversation with the user.

9. The non-transitory computer-readable storage medium of claim 1, wherein generating the search query based on the speech occurring prior to determining that the user is thinking the key thought comprises:
    converting the speech to text; and
    extracting one or more search terms from the text, wherein the search query includes the one or more search terms.

10. The non-transitory computer-readable storage medium of claim 1, wherein transmitting information received in response to the search query to the one or more output devices comprises:
    determining a time indicated by the user to transmit the information received in response to the search query; and
    transmitting the information received in response to the search query at the time indicated by the user to the one or more output devices.

11. The non-transitory computer-readable storage medium of claim 10, wherein transmitting information received in response to the search query to the one or more output devices comprises:
- determining an output time that comprises one of a time when no speech is detected, a time immediately after receiving the information in response to the search query, or a time when a cognitive load on the user is less than a threshold level; and
- transmitting the information received in response to the search query at the output time.

12. The non-transitory computer-readable storage medium of claim 1, wherein transmitting the information received in response to the search query to the one or more output devices comprises one of transmitting the information received in response to the search query to an output device that privately outputs information to the user or transmitting the information received in response to the search query to an output device that publicly outputs information.

13. A method for providing information based on neural activity, the method comprising:
- detecting speech;
- detecting a first neural activity of a user via one or more neural sensors that measure neural activity of one or more brain regions of the user;
- determining, via a neural analysis application, that the user is thinking a key thought based on the detected first neural activity, wherein the neural analysis application analyzes the first neural activity to determine that the first neural activity is associated with the user thinking the key thought, wherein the neural analysis application is configured to differentiate the first neural activity from other neural activity of the user;
- in response to determining that the user is thinking the key thought, generating a search query based on the speech occurring during a predetermined time period prior to determining that the user is thinking the key thought;
- receiving information based on the search query; and
- transmitting the information to an output device that privately outputs information to the user.

14. The method of claim 13, wherein generating the search query based on the speech occurring prior to determining that the user is thinking the key thought comprises:
- converting the speech to text; and
- identifying one or more questions in the text.

15. The method of claim 13, further comprising:
- detecting a second neural activity of the user;
- determining that the user is thinking a second key thought based on the detected second neural activity; and
- in response to determining that the user is thinking a second key thought, performing one of a fact-checking functions on speech occurring prior to determining that the user is thinking the second key thought or recording speech occurring prior to determining that the sure is thinking the second key thought.

16. A system, comprising:
- a neural sensor included in a head-worn assembly; and
- a processor coupled to the neural sensor and configured to:
  - detect speech;
  - detect a first neural activity of a user via the neural sensor that measures neural activity of one or more brain regions of the user;
  - determine, via a neural analysis application, that the user is thinking a key thought based on the detected first neural activity, wherein the neural analysis application analyzes the first neural activity to determine that the first neural activity is associated with the user thinking the key thought, wherein the neural analysis application is configured to differentiate the first neural activity from other neural activity of the user;
  - in response to determining that the user is thinking the key thought, generate a search query based on the speech occurring during a predetermined time period prior to determining that the user is thinking the key thought;
  - receive information based on the search query; and
  - transmit the information to an output device.

17. The system of claim 16, wherein the neural sensor includes an electroencephalography (EEG) device.

18. The system of claim 16, wherein the head-worn assembly comprises one of a headphone-based assembly or an earbud-based assembly.

19. The system of claim 16, wherein the output device comprises one of a loudspeaker included in the head-worn assembly or a display device included in the head-worn assembly.

* * * * *

UNITED STATES PATENT AND TRADEMARK OFFICE
CERTIFICATE OF CORRECTION

PATENT NO. : 11,144,596 B2  
APPLICATION NO. : 16/044438  
DATED : October 12, 2021  
INVENTOR(S) : Verbeke et al.

Page 1 of 1

It is certified that error appears in the above-identified patent and that said Letters Patent is hereby corrected as shown below:

In the Claims

Column 22, Claim 15, Line 6, please delete "a" and insert --the--;

Column 22, Claim 15, Line 8, please delete "functions" and insert --function--;

Column 22, Claim 15, Line 10, please delete "sure" and insert --user--.

Signed and Sealed this  
Twenty-first Day of December, 2021

Drew Hirshfeld  
*Performing the Functions and Duties of the*  
*Under Secretary of Commerce for Intellectual Property and*  
*Director of the United States Patent and Trademark Office*